US00PP34464P2

(12) United States Plant Patent
Mazzardis

(10) Patent No.: US PP34,464 P2
(45) Date of Patent: Aug. 2, 2022

(54) BLUEBERRY PLANT NAMED 'NS 15-15'

(50) Latin Name: ***Vaccinium* hybrid**
Varietal Denomination: 'NS 15-15'

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 17/497,321

(22) Filed: Oct. 8, 2021

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

| | | | |
|---|---|---|---|
| PP25,858 | P3 | 9/2015 | Mazzardis |
| PP25,859 | P3 | 9/2015 | Mazzardis |
| PP25,860 | P3 | 9/2015 | Mazzardis |
| PP25,889 | P3 | 9/2015 | Mazzardis |
| PP26,172 | P3 | 12/2015 | Mazzardis |
| PP26,173 | P3 | 12/2015 | Mazzardis |
| PP27,142 | P3 | 9/2016 | Mazzardis |
| PP28,149 | P3 | 7/2017 | Mazzardis |
| PP28,217 | P3 | 7/2017 | Mazzardis |
| PP28,334 | P3 | 8/2017 | Mazzardis |
| PP28,357 | P3 | 9/2017 | Mazzardis |
| PP28,358 | P3 | 9/2017 | Mazzardis |
| PP30,626 | P3 | 7/2019 | Mazzardis |
| PP30,755 | P3 | 7/2019 | Mazzardis |
| PP30,756 | P3 | 7/2019 | Mazzardis |
| PP30,846 | P2 | 8/2019 | Mazzardis |
| PP30,934 | P3 | 10/2019 | Mazzardis |
| PP32,745 | P3 | 1/2021 | Mazzardis |
| PP32,781 | P3 | 2/2021 | Mazzardis |
| PP32,823 | P3 | 2/2021 | Mazzardis |
| PP32,897 | P3 | 3/2021 | Mazzardis |
| PP33,087 | P3 | 5/2021 | Mazzardis |
| PP33,154 | P3 | 5/2021 | Mazzardis |
| PP33,112 | P3 | 6/2021 | Mazzardis |
| PP33,137 | P3 | 6/2021 | Mazzardis |
| PP33,138 | P3 | 6/2021 | Mazzardis |
| PP33,384 | P3 | 8/2021 | Mazzardis |
| PP33,494 | P3 | 9/2021 | Mazzardis |

OTHER PUBLICATIONS

Mazzardis, U.S. Appl. No. 17/336,801, filed Jun. 2, 2021.
Mazzardis, U.S. Appl. No. 17/487,468, filed Sep. 28, 2021.

*Primary Examiner* — Keith O. Robinson
(74) *Attorney, Agent, or Firm* — Randall Danskin, P.S.

(57) ABSTRACT

A new and distinct variety of blueberry plant, which is denominated varietally as 'NS 15-15' is described, with an upright plant growth habit and which produces fruit considered very large in size, firm, and low to medium in acidity under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 15-15'.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 15-15' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-50' (U.S. Plant Pat. No. 28,357) during the 2013 growing season.

Prior Varieties. The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time, a medium fruit cluster density, and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-50', on the other hand, is characterized principally by a semi-upright to intermediate growth habit, a medium vigor, a very early season first pick date, and further produces large- to very-large-sized, firm to very firm, high to very high sweetness, and low acidity fruit under the ecological conditions occurring in Yanchep, Western Australia. Also, the pollen parent 'EB 8-50' exhibits a very early date of bloom time, a dense fruit cluster density, and a December last pick date under the ecological conditions occurring in Yanchep, Western Australia. Further, the pollen parent 'EB 8-50' is evergreen and produces fruit on one-year-old and current season's shoots.

Origin. The seed from the seed parent 'EB 9-4' produced approximately 1,100 plants following cross-pollination. These new plants were then grown at the aforementioned property, and fruit from these new plants was first observed in 2015. A subsequent assessment of these same self-fertile, new plants conducted during the 2016 growing season led to selecting the 'NS 15-15' variety for additional evaluation in 2018, which led to selection for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 15-15' variety was a distinct and new variety of blueberry plant found to be true to the original plant. The new variety of blueberry plant was considered to be novel in view of its upright growth habit, very large fruit size, firm fruit, and low to medium fruit acidity.

Comparisons. In comparison to the seed parent 'EB 9-4' under the ecological conditions occurring in Yanchep, Western Australia, the new variety is noteworthy. In this regard, the seed parent has a plant growth habit considered to be semi-upright to intermediate. In contrast, the new variety of blueberry plant has a plant growth habit considered to be upright. In addition, the seed parent produces fruit with a size considered to be large to very large. This is in contrast to the fruit of the new variety of blueberry plant, which is considered to be very large in size. Also, the seed parent and the new variety of blueberry plant both produce fruit considered to be firm. Further, the seed parent and the new variety of blueberry plant both produce fruit considered to be low to medium in acidity.

In comparison to the pollen parent 'EB 8-50' under the ecological conditions occurring in Yanchep, Western Australia, the new variety is noteworthy. In this regard, the pollen parent has a plant growth habit considered to be semi-upright to intermediate. In contrast, the new variety of blueberry plant has a plant growth habit considered to be upright. In addition, the pollen parent produces fruit with a size considered to be large to very large. This is in contrast to the fruit of the new variety of blueberry plant, which is considered to be very large in size. Also, the pollen parent produces fruit considered to be firm to very firm. This is in contrast to the fruit of the new variety of blueberry plant, which is considered to be firm. Further, the pollen parent produces fruit considered to be low in acidity. This is in contrast to the fruit of the new variety of blueberry plant, which is considered to be low to medium in acidity.

The new variety of blueberry plant is readily distinguishable from the most closely related, known variety, the 'NS 16-18' blueberry plant described in U.S. Plant Pat. No. 33,494. In this regard, both the closest known variety 'NS 16-18' and the new variety of blueberry plant have a plant growth habit considered to be upright. In addition, the closest known variety 'NS 16-18' produces fruit with a size considered to be large to very large. This in contrast to the fruit of the new variety of blueberry plant, which is considered to be very large in size. Also, the closest known variety 'NS 16-18' produces fruit considered to firm to very firm. This is in contrast to the fruit of the new variety of blueberry plant, which is considered to be firm. Further, the closest known variety 'NS 16-18' produces fruit considered to be medium to high in acidity. This is in contrast to the fruit of the new variety of blueberry plant, which is considered to be low to medium in acidity.

The comparisons described above are summarized in Table 1 below.

TABLE 1

Summary of Comparisons

| | 'NS 15-15' | 'NS 16-18' | 'EB 9-4' (Seed) | 'EB 8-50' (Pollen) |
|---|---|---|---|---|
| Plant growth habit | Upright | Upright | Semi-upright to intermediate | Semi-upright to intermediate |
| Fruit size | Very large | Large to very large | Large to very large | Large to very large |
| Fruit firmness | Firm | Firm to very firm | Firm | Firm to very firm |
| Fruit acidity | Low to medium | Medium to high | Low to medium | Low |

In addition, Table 2 below compares the 'NS 15-15' variety to sibling cultivars that resulted from the same seed parent 'EB 9-4' and pollen parent 'EB 8-50', namely, 'NS 16-2' (U.S. Plant Pat. No. 32,897), 'NS 16-18' (U.S. Plant Pat. No. 33,494), and 'NS 15-14' (U.S. Plant application Ser. No. 17/487,468).

TABLE 2

Comparison to Sibling Cultivars

| | 'NS 15-15' | 'NS 16-2' | 'NS 16-18' | 'NS 15-14' |
|---|---|---|---|---|
| Plant growth habit | Upright | Semi-upright | Upright | Upright |
| Fruit size | Very large | Very large | Large to very large | Very large |
| Fruit firmness | Firm | Very firm | Firm to very firm | Medium |
| Fruit acidity | Low to medium | Low | Medium to high | Low |
| Plant vigor | Medium | Medium | Weak to medium | Weak to medium |
| Fruit sweetness | Medium to high | Medium to high | Medium | Medium to high |

BRIEF DESCRIPTION OF THE DRAWINGS

The accompanying drawings are color photographs of the new blueberry plant 'NS 15-15' during the third year of growth under the ecological conditions prevailing at the breeder's property, which is located at Yanchep Springs in Yanchep, Western Australia.

Figure 1:
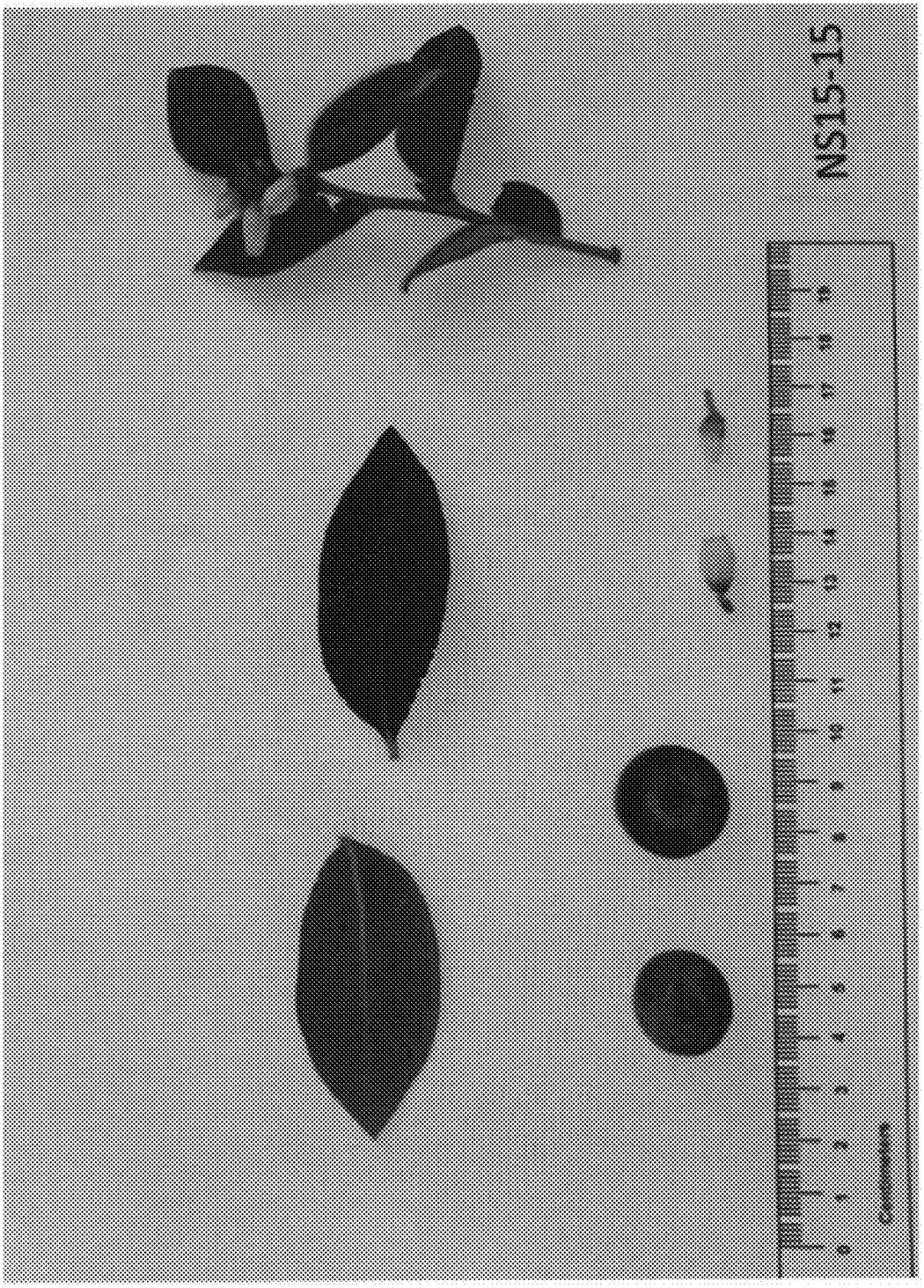
FIG. 1 is a color photograph, which shows fruit, blooms, leaves, and a portion of a vegetative stem of the new blueberry plant 'NS 15-15', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
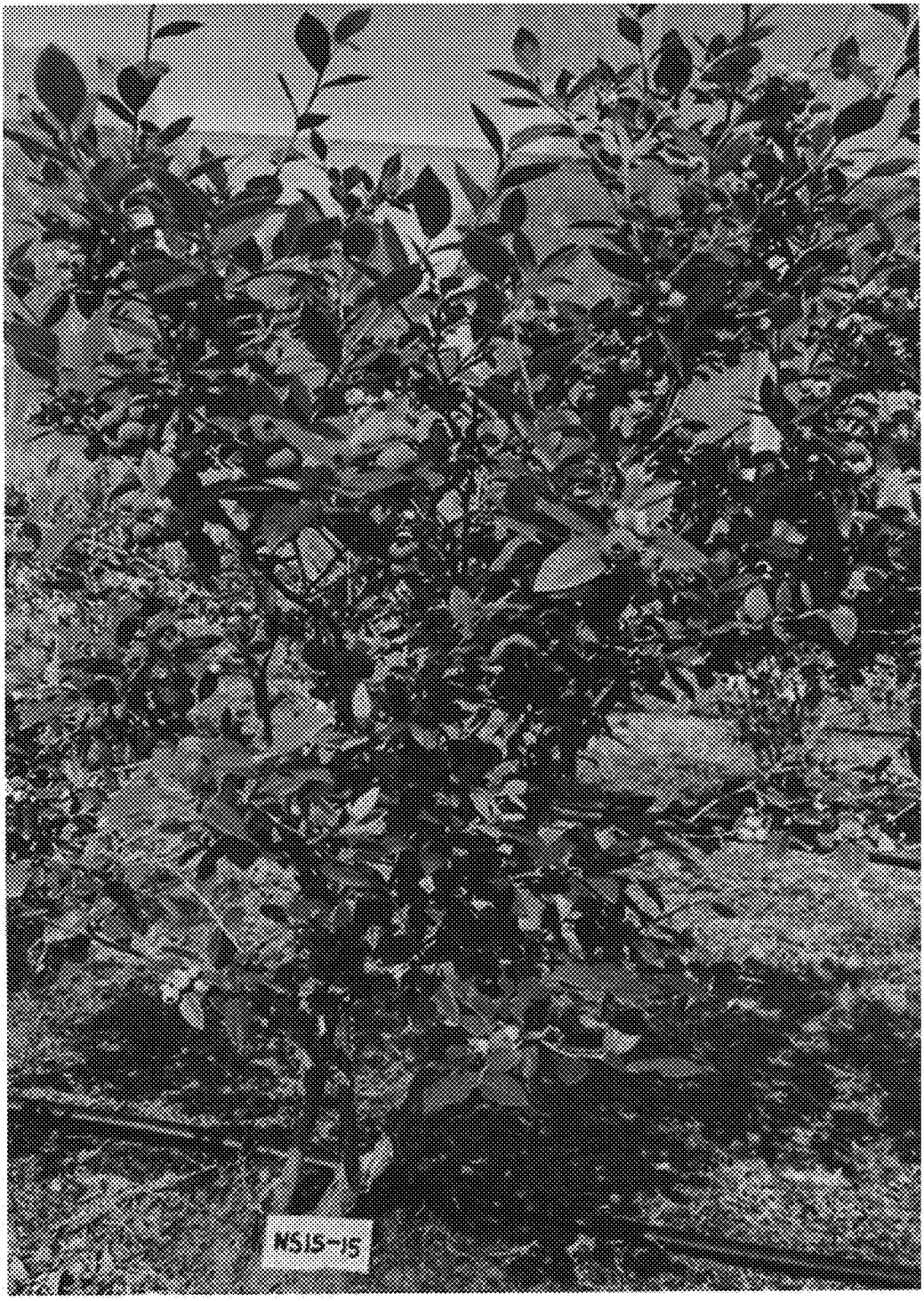
FIG. 2 is a color photograph, which shows the new blueberry plant 'NS 15-15.' This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor*.—Considered medium for the species.

*Growth habit*.—Considered upright. This is in contrast to the seed parent 'EB 9-4' and the pollen parent 'EB 8-50', wherein the growth habit is considered to be semi-upright to intermediate. This is comparable to the closest known variety 'NS 16-18', wherein the growth habit is also considered to be upright.

*Average size of plant*.—1.2 meters in height by 0.75 meters in width.

*Internode length* (*space between nodes*).—Considered medium, 22.41 millimeters (mm).

*Bark color*.—RHS Light Reddish Brown Group 177C.

*Color, one year old shoots*.—RHS Greyish Red Group 182B.

*Fruiting type*.—On one-year-old shoots and current season's shoots.

Foliage: General.

*Average leaf length*.—Considered medium to long for the species, 60.89 mm.

*Average leaf width*.—Considered medium to broad for the species, 30.48 mm.

*Color of leaf upper*.—RHS Greyish Olive Green Group NN137A.

*Color of leaf underside*.—RHS Greyish Yellow Green Group 191A.

*Vein color of plant leaf*.—RHS Light Yellow Green Group 145C.

*Venation pattern of leaf*.—Pinnate reticulate.

*Leaf apex texture*.—Glabrous.

*Leaf apex shape*.—Acute.

*Leaf base shape*.—Acute.

*Leaf shape*.—Elliptic.

*Leaf margin*.—Entire.

*Leaf arrangement of plant*.—Alternate.

*Petiole length*.—4.37 mm.

*Petiole diameter*.—2.34 mm.

*Petiole color*.—RHS Light Yellow Green 145C.

Flowers:

*Number of flowers/inflorescence*.—4.

*Length of inflorescence* (*excluding pedicel*).—Considered long, 10.52 mm.

*Infructescence density*.—Considered medium.

*Corolla shape*.—Urceolate.

*Corolla tube surface texture*.—Ridges are present on the corolla tube.

*Average corolla length*.—10.52 mm.

*Corolla diameter*.—9.56 mm.

*Corolla aperture size*.—4.15 mm.

*Corolla color*.—RHS White Group NN155B.

*Conspicuousness of ridges on corolla tube*.—Considered medium.

*Pedicel color*.—RHS Moderate Yellow Green Group 146B.

*Pedicel length*.—4.65 mm.

*Average calyx diameter*.—Considered small, 2.97 mm.

*Average calyx basin depth*.—Considered medium, 2.36 mm.

*Attitude of sepals*.—Erect.

*Type of sepals*.—Reflexed.

*Color of receptacle*.—RHS Moderate Yellow Green Group 146B.

Reproductive organs:

*Size of pollen anthers*.—7.36 mm.

*Color of pollen anthers*.—RHS Brownish Orange Group N167A.

*Pistil length*.—9.35 mm.

*Pistil color*.—RHS Light Yellow Green Group 145B.

Fruit:

*Color of unripe fruit*.—RHS Strong Yellow Green Group 144A.

*Color of fruit skin*.—RHS Bluish Black Group 203C at time of bloom removal.

*Color of ripe fruit flesh*.—RHS Light Yellow Green Group 145B.

*Color of seeds*.—RHS Brownish Orange Group N167A.

*Average fruit size*.—Very large, 20-22 mm in diameter and 13.83 mm in height. This is in contrast to the seed parent 'EB 9-4', the pollen parent 'EB 8-50', and the closest known variety 'NS 16-18', wherein the fruit size is considered large to very large.

*Average weight of fruit*.—2.5 grams.

*Fruit height/width ratio*.—Considered medium.

*Berry shape*.—Considered oblate.

*Sweetness when ripe*.—Considered medium to high for the species.

*Firmness when ripe*.—Considered firm for the species. This is comparable to the seed parent 'EB 9-4', wherein the fruit firmness is also considered firm. This is in contrast to the pollen parent 'EB 8-50' and the closest known variety 'NS 16-18', wherein the fruit firmness is considered firm to very firm.

*Acidity when ripe*.—Considered low to medium for the species. This is comparable to the seed parent 'EB 9-4', wherein the fruit acidity is also considered low to medium. This is in contrast to the pollen parent 'EB 8-50', wherein the fruit acidity is considered low. This is also in contrast to the closest known variety 'NS 16-18', wherein the fruit acidity is considered medium to high.

*Cluster density*.—Considered medium for the species.

*Average fruit production*.—3.5 kilograms on a two-year-old bush.

*Storability of fruit*.—Considered excellent for the species.

*Market use of fruit*.—1st grade fresh market fruit.

*Date of bud burst*.—This variety is evergreen under the ecological conditions prevailing in Yanchep, Western Australia, but a bud break occurs in August, which is considered medium in timing.

*Date of bloom time*.—This variety is evergreen under the ecological conditions prevailing in Yanchep, Western Australia, but a bloom time occurs in May, which is considered early on one-year-old shoots and is considered early on current year's shoots.

*Duration of bloom time and bloom intensity*.—4-6 weeks; bloom intensity is considered strong.

*Beginning of fruit ripening*.—Considered very early on one-year-old shoot and very early on current year's shoots.

*First pick date*.—The observed date of the first pick is approximately August under the ecological conditions prevailing in Yanchep, Western Australia.

*Last pick date*.—The observed date of the last pick is approximately October under the ecological conditions prevailing in Yanchep, Western Australia.

*Pollination requirements*.—Self-fertile.

*Resistance to pests and disease*.—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant named 'NS 15-15', substantially as illustrated and described, which is characterized principally as to novelty by an upright plant growth habit and by producing fruit considered very large in size, firm, and low to medium in acidity under the ecological conditions prevailing in Yanchep, Western Australia.

* * * * *